(12) United States Patent
Chen et al.

(10) Patent No.: US 11,364,031 B2
(45) Date of Patent: Jun. 21, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Wangdong Chen, Jiangsu (CN); Yi Guo, Jiangsu (CN); Zhi Chen, Jiangsu (CN); Jiang Lin, Jiangsu (CN); Xiaowei Xu, Jiangsu (CN)

(73) Assignee: TOUCHSTONE INTERNATIONAL MEDICAL SCIENCE CO., LTD.

( * ) Notice: Subject to any disclaimer, the term of this patent is extended or adjusted under 35 U.S.C. 154(b) by 155 days.

(21) Appl. No.: 16/957,587

(22) PCT Filed: Dec. 19, 2018

(86) PCT No.: PCT/CN2018/121973
§ 371 (c)(1),
(2) Date: Jun. 24, 2020

(87) PCT Pub. No.: WO2019/128792
PCT Pub. Date: Jul. 4, 2019

(65) Prior Publication Data
US 2020/0345372 A1    Nov. 5, 2020

(30) Foreign Application Priority Data

Dec. 26, 2017   (CN) .......................... 201711435644.3
Dec. 26, 2017   (CN) .......................... 201721846889.0

(51) Int. Cl.
*A61B 17/068*   (2006.01)
*A61B 17/115*   (2006.01)
(Continued)

(52) U.S. Cl.
CPC ....... *A61B 17/1155* (2013.01); *A61B 17/1114* (2013.01); *A61B 17/326* (2013.01);
(Continued)

(58) Field of Classification Search
CPC ........ A61B 2017/00367; A61B 17/068; A61B 17/115
(Continued)

(56) References Cited

U.S. PATENT DOCUMENTS 5,240,163 A  *  8/1993  Stein .................... A61B 17/072
                                                            227/175.3
5,318,221 A  *  6/1994  Green .............. A61B 17/07207
                                                            227/178.1
(Continued)

FOREIGN PATENT DOCUMENTS

CN     103142278 A     6/2013
CN     106388948 A     2/2017
(Continued)

OTHER PUBLICATIONS

International Search Report regarding related App. No. PCT/CN2018/121973; dated Feb. 27, 2019.
(Continued)

*Primary Examiner* — Gloria R Weeks
(74) *Attorney, Agent, or Firm* — Dickinson Wright PLLC

(57) ABSTRACT

A handle assembly and a stapler including the same are provided. The handle assembly includes a first handle, a second handle, a slot provided in the second handle and a slider slidably located in the slot. When the slider is in the first section of the slot, the first handle and the second handle are not linked; when the slider is in the second section of the slot, the first handle is linked to the second handle and actuates the second handle to move from an insurance position to a firing position. Therefore, only the movement
(Continued)

of the second handle can fire the stapler. No matter whether the stapler is ready to be fired or not, the first handle can be pressed by the doctor, while the stapler cannot be fired when the stapler is not ready to be fired.

18 Claims, 15 Drawing Sheets

(51) Int. Cl.
  *A61B 17/11* (2006.01)
  *A61B 17/326* (2006.01)
  *A61B 17/00* (2006.01)
  *A61B 17/072* (2006.01)

(52) U.S. Cl.
  CPC ............ *A61B 2017/00367* (2013.01); *A61B 2017/07257* (2013.01); *A61B 2017/07271* (2013.01); *A61B 2017/07285* (2013.01)

(58) Field of Classification Search
  USPC .................................................. 227/175.2
  See application file for complete search history.

(56) References Cited

U.S. PATENT DOCUMENTS

| | | | | |
|---|---|---|---|---|
| 5,782,396 | A * | 7/1998 | Mastri | A61B 17/07207 227/175.3 |
| 8,695,866 | B2 * | 4/2014 | Leimbach | A61B 17/10 227/175.2 |
| 8,733,611 | B2 * | 5/2014 | Milliman | A61B 17/068 227/175.2 |
| 9,700,341 | B2 * | 7/2017 | Conlon | A61B 17/320068 |
| 9,861,358 | B2 * | 1/2018 | Marczyk | A61B 17/07207 |
| 10,441,272 | B2 * | 10/2019 | Gustafson | A61B 17/06133 |
| 10,478,189 | B2 * | 11/2019 | Bear | H02J 7/00 |
| 2009/0206123 | A1 | 8/2009 | Doll | |
| 2010/0051669 | A1 | 3/2010 | Milliman | |
| 2013/0153630 | A1 | 6/2013 | Miller | |
| 2017/0181748 | A1 | 6/2017 | Hessler et al. | |
| 2017/0348002 | A1 | 12/2017 | Murugesan | |

FOREIGN PATENT DOCUMENTS

| | | |
|---|---|---|
| CN | 206261635 U | 6/2017 |
| CN | 107106180 A | 8/2017 |
| CN | 107485429 A | 12/2017 |
| JP | S6148345 A | 3/1986 |
| JP | 61048345 U | 4/1986 |
| JP | H05212041 A | 8/1993 |
| JP | 3148464 U | 2/2009 |
| JP | 2009189831 A | 8/2009 |
| JP | 2015503949 A | 2/2015 |
| JP | 2017099988 A | 6/2017 |
| RU | 2013145706 A | 4/2015 |

OTHER PUBLICATIONS

Office Action regarding corresponding JP App. No. 2020-533575; dated Jun. 24, 2021.
European Search Report regarding corresponding EP App. No. 18894614; dated Sep. 10, 2021.
Examination Report No. 1 regarding corresponding AU Pat. App. No. 2018393359; dated Oct. 16, 2020.
Communication regarding corresponding RU App. No. 2020124400/14; dated Oct. 23, 2020.
Office Action regarding corresponding JP App. No. 2020-533575; dated Jun. 29, 2021.

* cited by examiner

HANDLE ASSEMBLY AND STAPLER INCLUDING THE SAME

CROSS-REFERENCE TO RELATED APPLICATIONS

This application is based upon PCT patent application No. PCT/CN2018/121973, filed on Dec. 19, 2018, which claims priority to Chinese Patent Application No. 201711435644.3 and No. 201721846889.0, filed on Dec. 26, 2017, the entire contents of which are incorporated herein by reference.

TECHNICAL FIELD

The present disclosure relates to medical instruments' technology, more particularly, to stapler technology, and specifically to a handle assembly and a stapler including the same.

BACKGROUND

Digestive tract tumor is one of human diseases of high incidence. During treatment, a circular stapler is widely used for suturing physiological tissues such as tissues in the digestive tract, instead of the manual operation by doctors. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapler, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the distal end is an end closer to the operator, the proximal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the suturing operation.

Along with the technological development, the firing transmission mechanism of the circular stapler has been improved with a lockout mechanism added. Therefore, when the stapler is not ready to be fired, even the doctor presses the handle, the handle cannot be moved for the lockout mechanism, to prevent the stapler from being fired by mistake. However, in practice, the lockout mechanism has some defects. For example, the insurance mechanism has some negative impacts on the operators' experience, and the casing of the stapler may be cracked if the doctor presses the handle vigorously.

SUMMARY

In the light of the problems in the prior art, the object of the present disclosure is to provide a handle assembly and a stapler including the same, to realize that, the first handle can be pressed by the doctor to move no matter whether the stapler is ready to be fired or not, while, the stapler cannot be fired by the first handle through the second handle when the stapler is not ready to be fired, and to prevent the casing from being cracked by pressing the handle vigorously.

In the present disclosure, a handle assembly to fire the stapler is provided, includes: a first handle and a second handle; a slot, provided in the second handle and including a first section and a second section; and a slider, slidably located in the slot; wherein, when the slider is in the first section of the slot, and the first handle is rotated in a first direction, the slider is not in contact with the first handle, and the second handle is in an insurance position; when the slider is in the second section of the slot, and the first handle is rotated in the first direction, the slider is in contact with the first handle and actuates the second handle to move from the insurance position to a firing position.

In some embodiments, the handle assembly further includes:

an indicator, movable between a first position area and a second position area;

a rod, having a first end connected to the indicator.

In some embodiments, a second end of the rod is connected to the slider, when the indicator is moved from the first position area to the second position area, the indicator actuates the slider to move from the first section to the second section of the slot through the rod.

In some embodiments, the indicator is connected to a distal end of a pulling sheet, a proximal end of the pulling sheet is sleeved on a screw rod, and a distal end of the screw rod is connected to a knob, when the knob is rotated to pull the pulling sheet to move towards a proximal end of the stapler, the indicator is moved by the pulling sheet from the first position area to the second position area.

In some embodiments, the first handle is rotatably connected to the second handle through a first pin, and the second handle is rotatably connected to a casing of the stapler through a second pin.

In some embodiments, a first torsion spring and a second torsion spring are sleeved on the first pin and the second pin, respectively; two ends of the first torsion spring are in contact with the first handle and the second handle, respectively; two ends of the second torsion spring are in contact with the second handle and the casing of the stapler, respectively.

In some embodiments, the slider includes a slider butting portion and a rod connecting portion, the rod connecting portion is connected to a second end of the rod; when the slider is in the second section of the slot, and the first handle is rotated in a first direction, the first handle is in contact with the slider butting portion.

In some embodiments, the rod connecting portion includes a limit groove for the rod and a boss connected to the rod, the second end of the rod is inserted into the limit groove, and the rod is connected to the boss through a fastener.

In some embodiments, a pin-hole is provided on the boss, a connecting pin passes through the pin-hole, and the rod is rotatably connected to the boss through the connecting pin.

In some embodiments, the first handle includes a handle butting surface, the slider butting portion includes a slider butting surface, and when the first handle is in contact with the slider, the handle butting surface is parallel and fit to the slider butting surface.

In some embodiments, a groove for the rod is provided on the indicator, the first end of the rod is movably located in the groove for the rod.

In some embodiments, a groove for the indicator is provided on the rod, a first end of the indicator is movably located in the groove for the indicator.

In some embodiments, the first handle includes a first cavity having two side walls, and the second handle includes a second cavity having two side walls;

When the slider is in the first section of the slot, and the first handle is rotated in the first direction, the first handle at least partially enters into the second cavity; when the slider is in the second section of the slot, and the first handle is rotated in the first direction, end surfaces of the side walls of the first handle is in contact with the slider, to prevent the first handle from continuing to enter into the second cavity.

In some embodiments, a limit groove for the first torsion spring is provided on the slider, two ends of the first torsion spring are in contact with the inner surface of the limit groove for the first torsion spring and the first handle, respectively.

In some embodiments, the handle assembly further includes a return spring for the slider, when the slider is in the second section of the slot, the return spring is forced by the slider to be in a deformation state; when the return spring recovers from the deformation state to its initial state, the slider is actuated thereby to move from the second section to the first section of the slot.

In some embodiments, the return spring is a return torsion spring for the slider, a limit groove for the return torsion spring is provided on the slider, and two ends of the return torsion spring are in contact with the inner surface of the limit groove for the return torsion spring and the first handle.

In some embodiments, the slider further includes a slider butting portion and a rod connecting portion connected to a second end of the rod, the limit groove for the return torsion groove is located between the slider butting portion and the rod connecting portion; when the slider is in the second section of the slot, and the first handle is rotated in a first direction, the first handle is in contact with the slider butting portion.

In the present disclosure, a stapler is provided including the handle assembly as aforementioned.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

BRIEF DESCRIPTION OF THE DRAWINGS

Embodiments of the present disclosure will now be described, by way of example only, with reference to the accompanying schematic drawings, and the other technical features, objects and advantages will be more obvious.

DETAILED DESCRIPTION

In the following, embodiments of the present disclosure will be described in detail with reference to the figures. The concept of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to those skilled in the art fully. Same reference signs in the figures refer to same or similar elements, so repeated description of them will be omitted.

Figure 1:
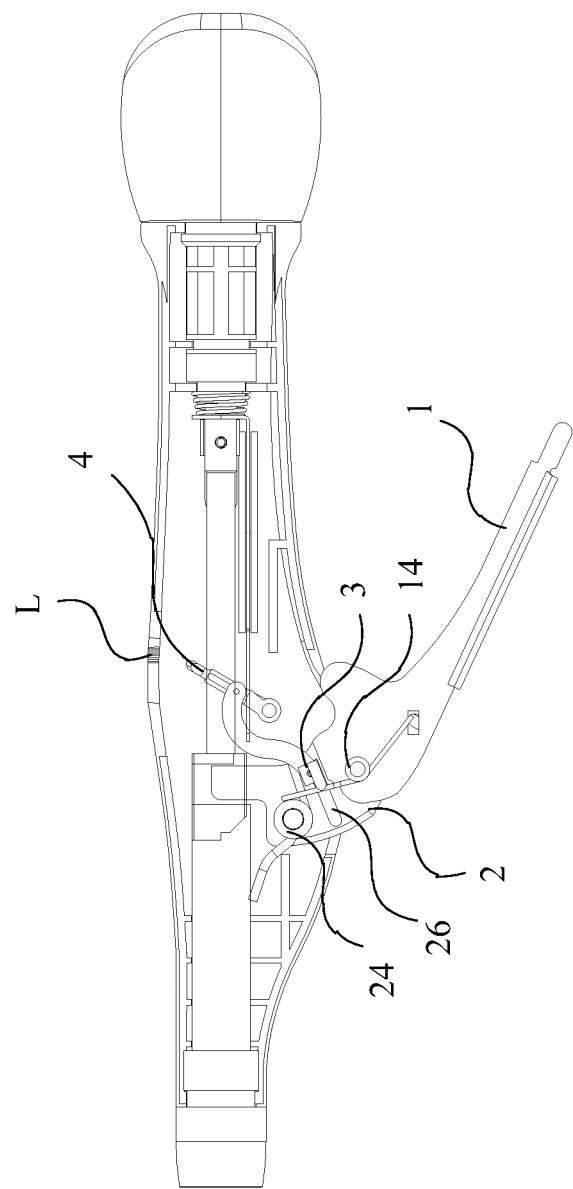
FIG. 1 is a schematic view of a handle assembly used for a stapler according to an embodiment of the present disclosure.

As shown in FIG. 1, to realize the object as aforementioned, a handle assembly for firing a stapler is provided according to an embodiment of the present disclosure. The handle assembly is divided into a first handle 1 and a second handle 2 (in FIG. 1, a casing of the handle assembly is omitted for clear presentation), and only the rotation of the second handle 2 can fire the stapler.

As shown in FIGS. 1-9, in the embodiment, the handle assembly further includes an indicator 4 having a first end 41 and a second end 42, the second end 42 is rotatably fixed to a casing of the stapler, and the first end 41 can be rotated around the second end 42. The first end 41 of the indicator 4 is connected to a distal end of a pulling sheet, and a proximal end of the pulling sheet is sleeved on a screw rod having a proximal end connected to a knob. When the knob is rotated, the first end 41 of the indicator can be pulled by the pulling sheet to move between a first position area and a second position area. A window is provided on the instrument body, between the first position area and the second position area, through which the position of the second end 42 of the indicator can be observed during operation. When the first end 41 of the indicator is in the first position area, the stapler is in an insurance state and not ready to be fired. When the first end 41 of the indicator is in the second position area, the stapler is ready to be fired. To give a more obvious indication to the doctor, the second position area L indicating the stapler being ready to be fired is a green area, which is already existed in the prior art. The handle assembly further includes a rod 5 having a first end 51 connected to the indicator 4. When the first end 41 of the indicator 4 is moved between the first position area and the second position area L, the rod 5 is moved by the indicator 4, thereby passing the moving to a second end 52 of the rod 5.

The first handle 1 includes a handle butting portion 16, a slot 26 and a slider 3 are provided on the second handle 2, the slider 3 is slidable in the slot 26, and the second end 52 of the rod 5 is connected to the slider 3. When the first end 41 of the indicator 4 is moved from the first position area to the second position area L, the slider 3 is actuated, by the indicator 4 through the rod 5, to move from the first section to the second section of the slot 26.

When the slider 3 is in the first section of the slot 26, and the first handle 1 is pressed to rotate in a first direction, the handle butting portion 16 is not in contact with the slider 3, and the second handle 2 is in an insurance position. When the slider 3 is in the second section of the slot 26, and the first handle 1 is pressed to rotate in a first direction, the handle butting portion 16 is in contact with the slider 3, and the second handle 2 is actuated, by the handle butting portion 16 through the slider, to move from the insurance position to a firing position. Then the second handle 2 pushes a staple pushing rod to fire the stapler. In the embodiment, the first direction refers to the anticlockwise direction shown in the FIGS. and the direction the handle moved along when pressed.

Figure 6:
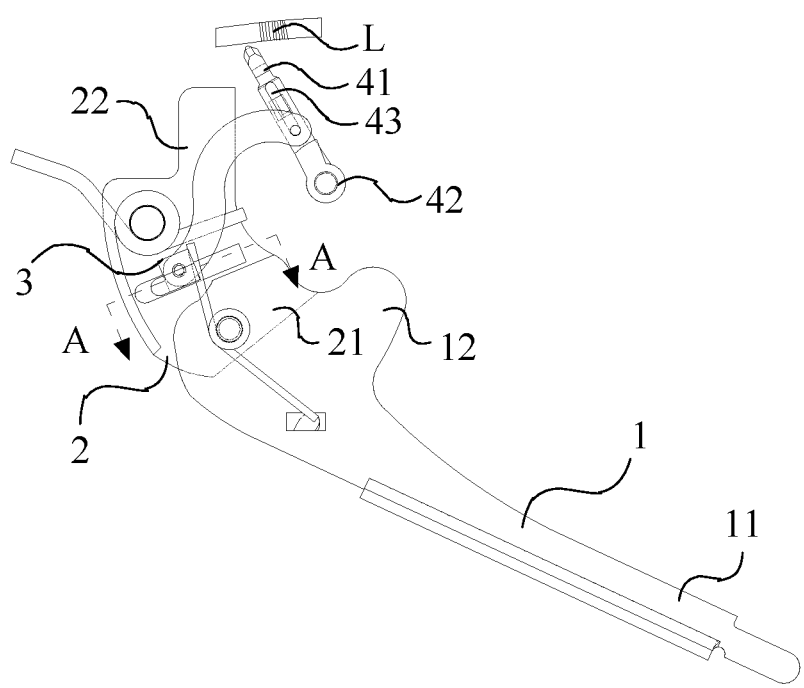
FIG. 6 is a schematic view of the handle assembly when the indicator is in a first position area, and the first handle is not rotated, according to the embodiment of the present disclosure.

It should be noted that, in the present disclosure, the first section and the second section of the slot 26 are relative concepts, and they do not always refer to two ends of the slot 26. As shown in FIG. 6, the first section is on the left side of the second section of the slot.

When the first end 41 of the indicator 4 is in the first position area and the second area L, the movement of the first handle 1 has different effects on the second handle 2. When the first end 41 of the indicator 4 is in the first position area, the movement of the first handle 1 will not force on the second handle 2, and the second handle 2 will not fire the stapler. When the first end 41 of the indicator 4 is in the second section L of the slot, and the first handle 1 is pressed to rotate anticlockwise, the second handle 2 is actuated thereby to push the staple pushing rod and fire the stapler. Therefore, by adjusting the position of the indicator 4, the cooperation relationship between the first handle 1 and the second handle 2 can be changed. Besides, the position of the indicator 4 also corresponds to the position relationship between a cartridge assembly and an anvil assembly of the stapler. When the first end of the indicator 4 is pulled by the pulling sheet to move to the second position area L, the anvil assembly is close to the cartridge assembly to realize an appropriate firing distance.

Above all, when the stapler is not ready to be fired, the first end 41 of the indicator 4 is in the first position area. At this time, if the doctor presses the first handle 1, the first handle 1 can be rotated easily, while the second handle 2 won't be actuated. As the stapler is in an invalid firing state, the first handle 1 can be rotated by a very small force. The doctor can also know the stapler is in the invalid firing state through the operation experience and the casing of the stapler will not be cracked. When the stapler is ready to be fired, the indicator 4 is in the second position area L. At this time, when the doctor presses the first handle 1, the first handle 1 will actuate the second handle 2 to move, thereby firing the stapler.

Figure 2:
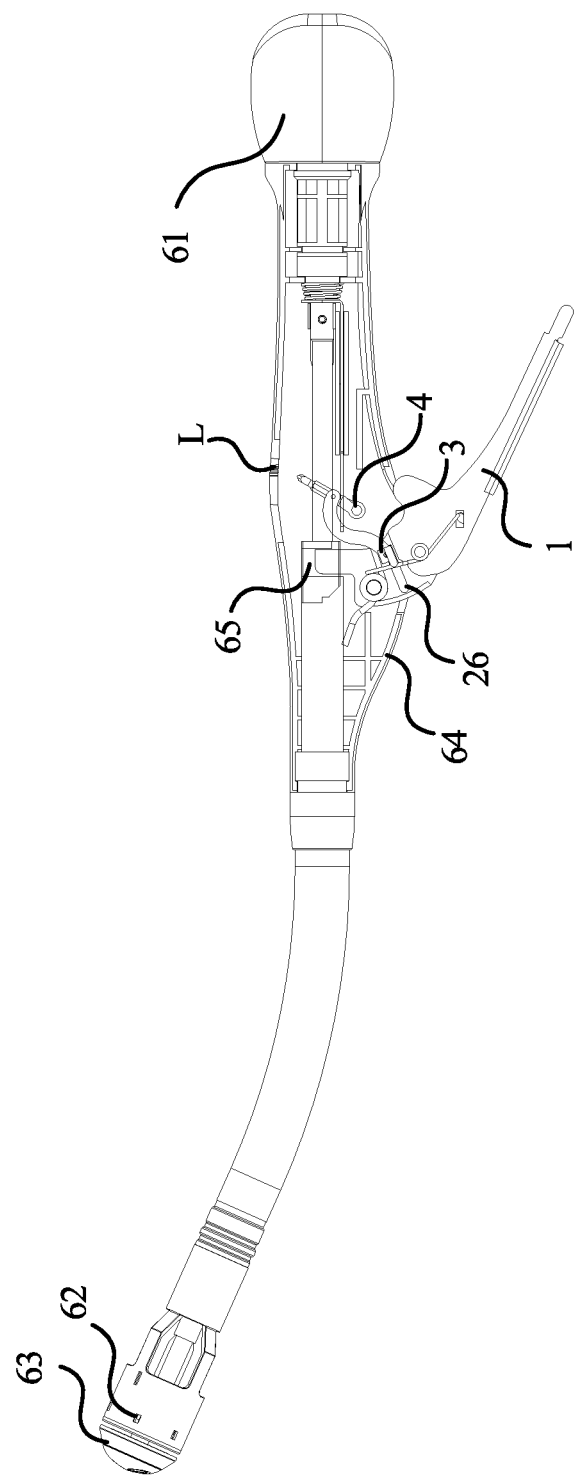
FIG. 2 is a schematic view of a circular stapler according to the embodiment of the present disclosure.
Figure 3:
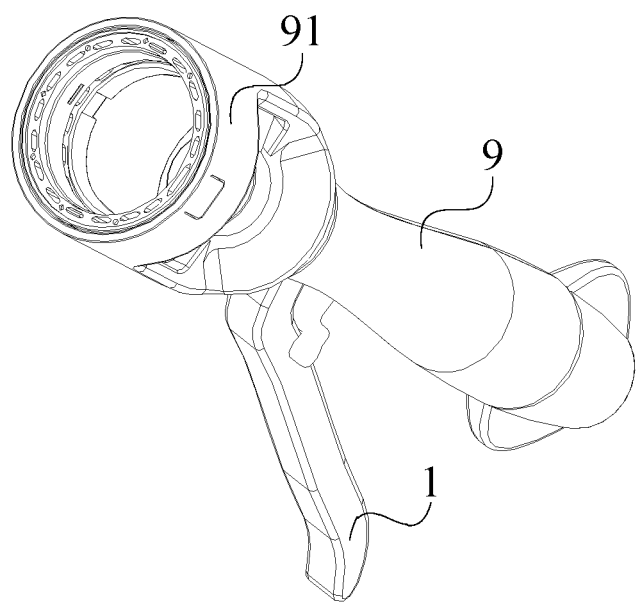
FIG. 3 a schematic view of the handle assembly used for a circumcision stapler according to the embodiment of the present disclosure.

FIG. 2 is a schematic view of the handle assembly used for a circular stapler according to the embodiment of the present disclosure. A cartridge assembly 62 and an anvil assembly 63 are provided on one end of the stapler, and a knob 61 and the handle assembly are provided on the other end of the stapler. The second end of the second handle 2 is cooperated with a staple pushing rod 65. When the stapler is ready to be fired, the second handle 2 pushes the staple pushing rod 65, to further push a staple pushing sheet and a circular cutter of the stapler, thereby cutting and suturing the tissues to be operated. FIG. 2 only shows the structure of the stapler as an example, in other embodiments, the handle assembly can also be used in other kinds of staplers to realize the object of the present disclosure. For example, FIG. 3 is a schematic view of an instrument body 9 of a circumcision stapler including the handle assembly. The instrument body 9 of the circumcision stapler is provided with a cartridge assembly 91 on a distal end thereof, and a glans cap (not shown in the FIGS) cooperated with the cartridge assembly 91. The second handle 2 is movably connected to one end of the circumcision stapler, the second end of the second handle 2 is cooperated with a staple pushing component of the circumcision stapler. When the stapler is ready to be fired, the staple pushing component is pushed by the second handle 2 to fire the circumcision stapler.

In the embodiment, a first end 11 of the first handle 1 is a holding portion. A second end 12 of the first handle 1 can be rotatably connected to a first end 21 of the second handle 2 through a first pin 14. A first torsion spring 15 sleeved on the first pin 14 is located between the first handle 1 and the second handle 2. Further, the second end 22 of the second handle 2 can be rotatably connected to the casing 64 of the staple through a second pin 24. A second torsion spring 25 is located between the second handle 2 and the casing 54 of the stapler, to automatically realize the return of the second handle 2 after being rotated.

Figure 4:
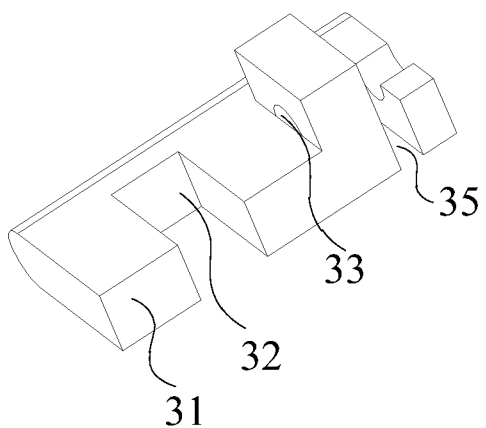
FIG. 4 is a schematic view of a slider according to the embodiment of the present disclosure.
Figure 8:
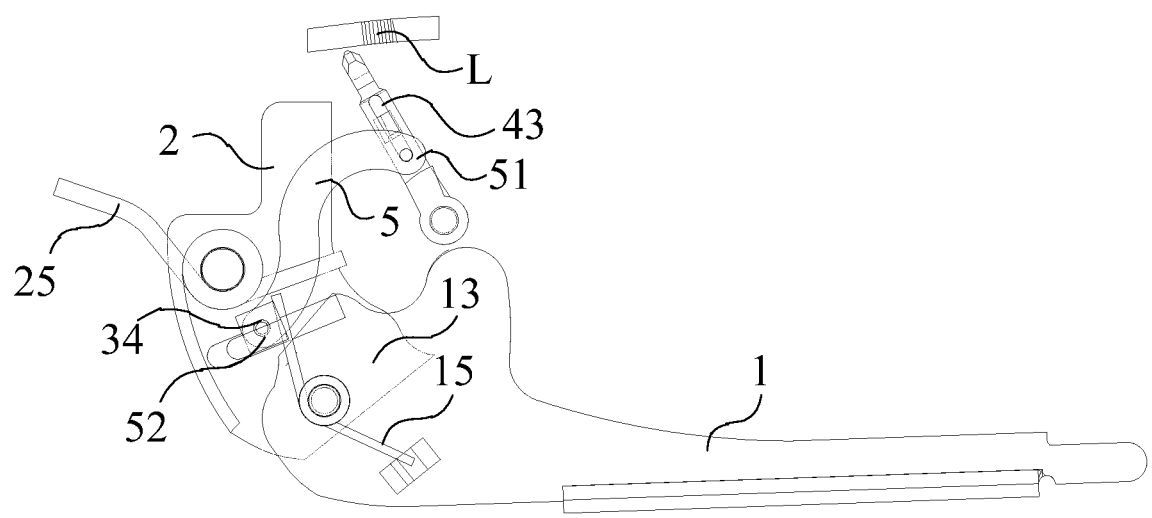
FIG. 8 is a schematic view of the handle assembly when the indicator is in a first position area, and the first handle is rotated, according to the embodiment of the present disclosure.

FIG. 4 and FIG. 8 are schematic views of the slider 3 according to the embodiment. The slider 3 includes a slider butting portion 31 and a rod connecting portion. When the slider 3 is in the second section of the slot 26, and the first handle 1 is pressed to be rotated anticlockwise, the handle butting portion 16 is in contact with the slider butting portion 31. The rod connecting portion includes a limit groove 35 for the rod and a boss to connect the rod, a pin-hole 33 is provided on the boss, the second end 52 of the rod 5 is located in the limit groove 35, and the rod 5 is connected to the boss through a connecting pin 34 passing through the pin-hole 33. The connecting structure of the rod 5 and the slider 3 is only described here as an example, in other embodiments, the rod 5 and the slider 3 can also be connected by other structures, for example, the connecting pin can be changed to a thread component or other fasteners, and other connecting structures are all included in the scope of the present disclosure.

The handle butting portion 16 includes a handle butting surface, the slider butting portion 31 includes a slider butting surface, and when the handle butting surface is in contact with the slider butting surface, the handle butting surface is fit to the slider butting surface, and the handle butting surface is preferably parallel to the slider butting surface, thereby maximizing the contacting surface of the two butting surfaces, and keeping a stable firing process. In other embodiments, the handle butting surface can also be not parallel to the slider butting surface. The other surface, opposite to the slider butting surface, of the slider butting portion 31 is in contact with the second handle 2. Therefore, when the slider butting surface is fit to the handle butting surface, the actuating force will be passed, from the handle butting portion 16 to the second handle 2, through the slider 3.

Further, a limit groove 32 for the torsion spring is provided in the slider 3. The first end of the first torsion spring 15 is located in the limit groove 32 for the torsion spring, and a second end of the first torsion spring 15 is in contact with the first handle 1. The limit groove 32 for the torsion spring is located between the slider butting portion 31 and the rod connecting portion. Therefore, the first torsion spring 15 can not only act as the return torsion spring for the first handle 1, but also act as the return torsion spring for the slider 3. When the first torsion spring 15 is in its normal state, the slider 3 is in the first section of the slot 26. When the slider 3 is moved to the second end of the slot 26, the first torsion spring 15 is deformed. After the external force on the slider 4 is released, the slider 3 can return to its initial position by a returning force of the first torsion spring 15.

Using first torsion spring 15 as a return torsion spring for the first handle 1 and the slider 3 at the same time can reduce the quantity of components, and simplify the structure. Considering the returning force for the first handle 1 is larger than that for the slider 3, another return spring only for the slider can be added. When the slider 3 is in the second section of the slot 26, the slider 3 forces the return spring for the slider to be in a deformation state, and when the return spring for the slider 3 is recovered from the deformation state to its initial state, the slider 3 is returned from the second section to the first section of the slot 26 by the return spring for the slider. In the embodiment, the return spring for the slider is a return torsion spring for the slider, two ends of the return torsion spring for the slider are in contact with the inner surface of the limit groove 32 and the first handle 1. In other embodiments, the return spring for the slider can also be an extension spring, a pressure spring, etc.

Figure 5:
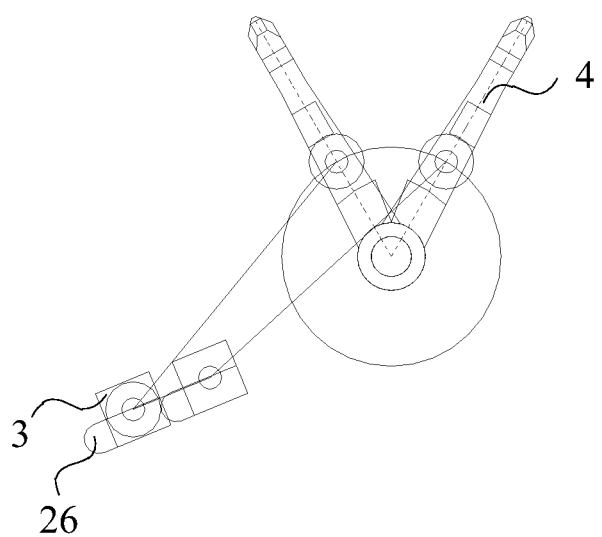
FIG. 5 is a schematic view showing the slider in different positions of a slot according to the embodiment of the present disclosure.

FIG. 5 is a schematic view showing the slider 3 in different positions of the slot 26 according to the embodiment. When the slider 3 is in the first section of the slot 26, i.e. a left position shown in FIG. 5, the stapler is in the insurance state. The slider 3 will not interfere with the handle butting portion 16. At this time, the first handle 1 can be pressed with a smaller force by the operator, to be rotated anticlockwise around the first pin 14, and the second handle 2 is not rotated. When the slider 3 is in the second section of the slot 26, i.e. a right position shown in FIG. 5, the slider 3 will interfere with the handle butting portion 16, and the first handle 1 actuates the second handle 2 to be rotated anticlockwise around the second pin 24.

Figure 7:
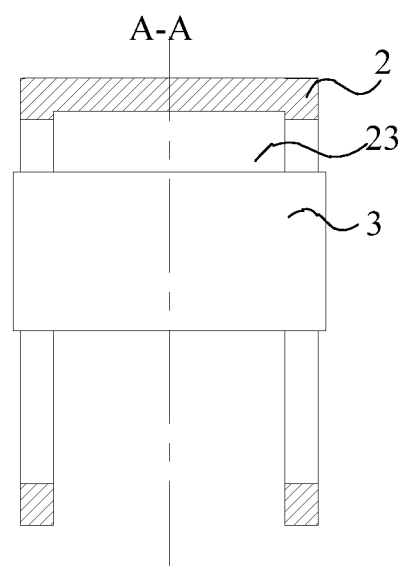
FIG. 7 is a section view along A-A direction of FIG. 6.

FIGS. 6-8 show the state of the handle assembly when the first end 41 of the indicator 4 is in the first position area. As shown in FIGS. 6 and 7, the first handle 1 is not pressed by the operator, and not be rotated. At this time, the slider 3 is kept in the first section of the slot 26, i.e. the left position in the FIGS, by the indicator 4 through the rod 5, and the slider 3 is not in contact with the handle butting portion 16. It should be noted that, the initial position of the slider 3 refers to the position located in the first section and far away from the second section of the slot. The slider 3 is kept in the initial position by the first torsion spring 15, a return torsion spring for the slider or the first end 41 of the indicator 4.

In the embodiment, a groove 43 for the rod is provided on the indicator 4, to provide space for the indicator 4 during rotation. The first end 51 of the rod 5 is movably located in the groove 43 for the rod.

As shown in FIGS. 7 and 8, in the embodiment, the first handle 1 selectively includes a first cavity 13 having two side walls, and the second handle 2 includes a second cavity 23 having two side walls. When the slider 3 is in the first section of the slot 26, and the first handle 1 is pressed to rotate anticlockwise, as the slider 3 is not in contact with the handle butting portion 16, the first handle 1 at least partially enters into the second cavity 23, and the fist handle 1 and the second handle 2 are not linked together. Therefore, the second handle 2 is kept in the initial insurance position. The handle can be pressed by the doctor without firing the stapler. As the first torsion spring 15 has a torsion force much less than the firing force, the doctor only needs to overcome the torsion force of the first torsion spring 15, the doctor can also get the tactile feedback to know that the indicator 4 is not in the second position area L and the stapler is not fired.

Figure 9:
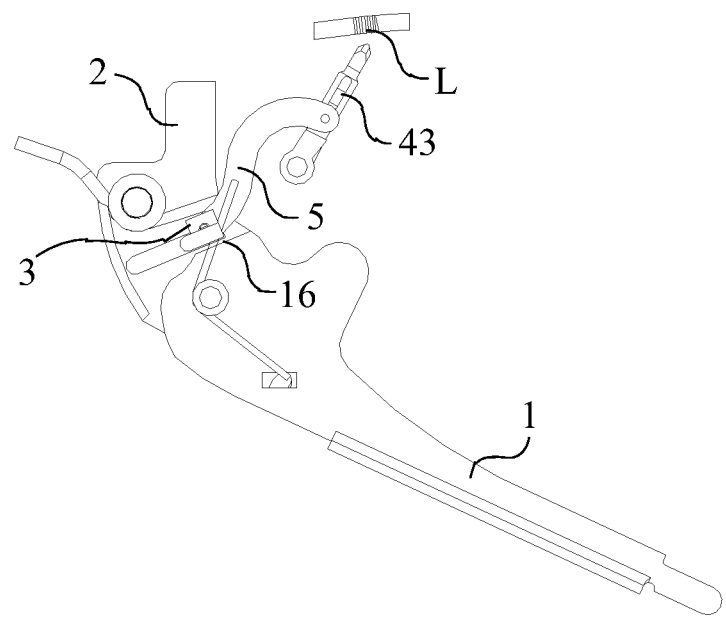
FIG. 9 is a schematic view of the handle assembly when the indicator is in a second position area, and the first handle is not rotated, according to the embodiment of the present disclosure.
Figure 10:
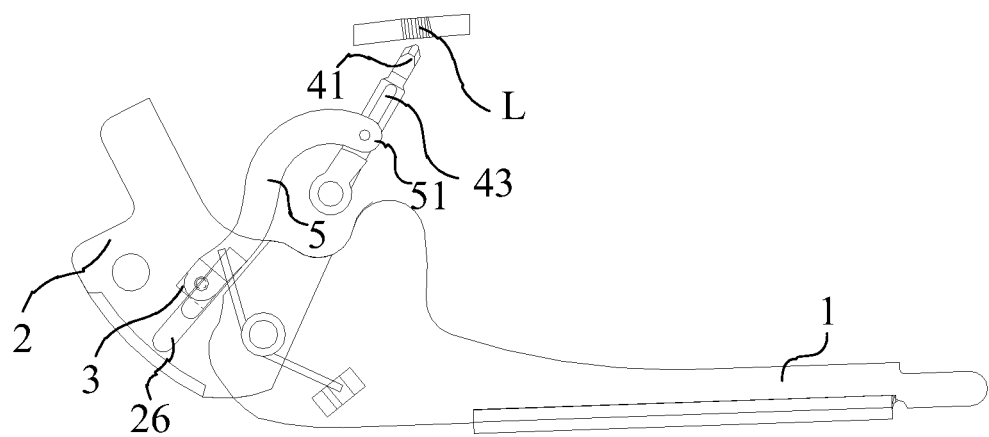
FIG. 10 is a schematic view of the handle assembly when the indicator is in the second position area, and the first handle is rotated, according to the embodiment of the present disclosure.

FIGS. 9 and 10 show the working state of the handle assembly when the indicator 4 is in the second position area. As the knob is rotated, the first end 41 of the indicator 4 is pulled by the pulling sheet, to the second position area L, the slider 3 is in the second section of the slot 26, and first handle 1 is not held.

As shown in FIG. 10, as the slider 3 is in the second section of the slot 26, the slider 3 will interfere with the handle butting portion 16. When the first handle 1 is pressed to rotate, the handle butting portion 16 is in contact with the slider 3, to link the first handle 1 and the second handle 2 together, to actuate the second handle 2 to rotate anticlockwise, thereby pushing the staple pushing rod 65 and firing the stapler. When the stapler is fired, the second end 12 of the first handle 1 is in contact with the pulling sheet when rotated, and lifts the pulling sheet to depart from the indicator 4, the indicator 4 is returned to its initial position by the indicator return mechanism. After the first handle 1 is released, the first handle 1 is returned to its initial state clockwise by the first torsion spring 15, the second handle 2 will return to its initial insurance position clockwise by the second torsion spring 25.

Figure 11:
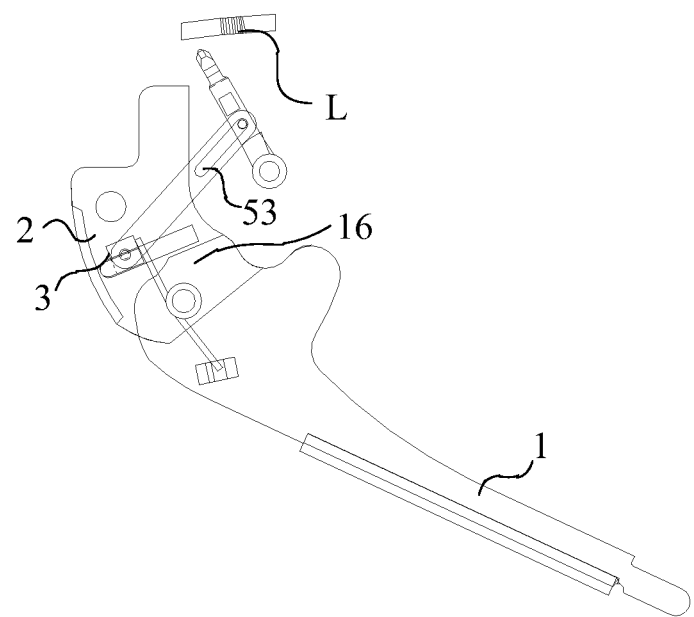
FIG. 11 is a schematic view of the handle assembly when the indicator is in the first position area, and the first handle is not rotated, according to another embodiment of the present disclosure.
Figure 12:
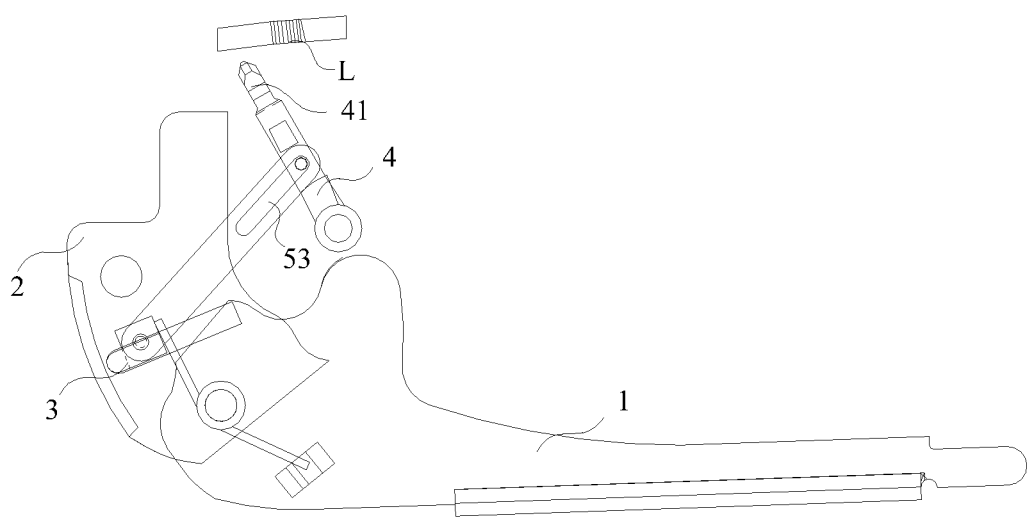
FIG. 12 is a schematic view of the handle assembly when the indicator is in the first position area, and the first handle is rotated, according to another embodiment of the present disclosure.

FIGS. 11 and 12 show the working state of the handle assembly according to another embodiment of the present disclosure. The difference between the embodiment and the last embodiment is that there is no groove for the rod provided on the indicator 4, while a groove 53 for the indicator is provided on the rod 5. The first end 41 of the indicator 4 is movably located in the groove 53 for the indicator.

As shown in FIG. 11, when the first end 41 of the indicator 4 is in the first position area, and the first handle 1 is not pressed, the slider 3 is in the first section of the slot 26, the slider 3 will not interfere with the handle butting portion 16, and the first handle 1 is not rotated. As shown in FIG. 12, when the first handle 1 is rotated, the handle butting portion 16 will not be in contact with the slider 3, the handle butting portion 16 can partially enter into the second cavity 23, and the first handle 1 and the second handle 2 are not linked together. Therefore, the second handle 2 is kept in its initial insurance position. At this time, the handle can be pressed by the doctor without firing the stapler.

Figure 13:
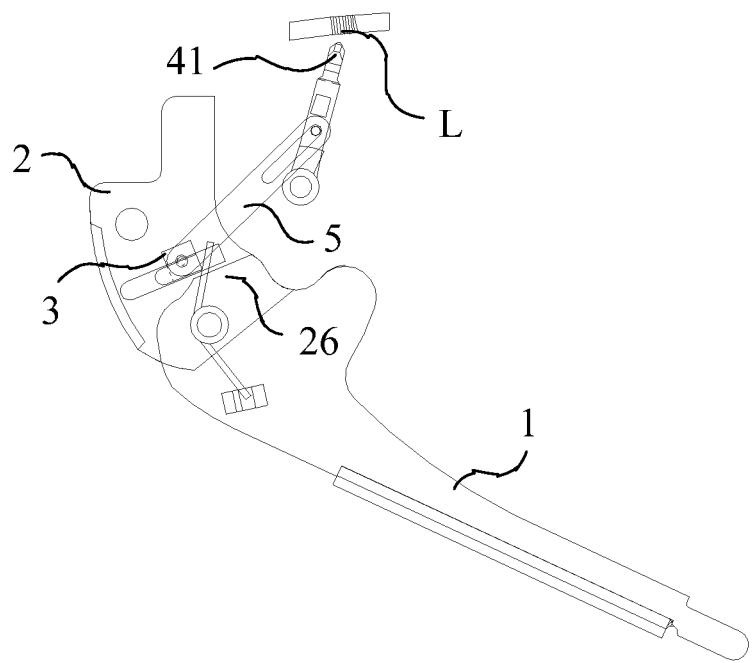
FIG. 13 is a schematic view of the handle assembly when the indicator is in the second position area, and the first handle is not rotated, according to another embodiment of the present disclosure.
Figure 14:
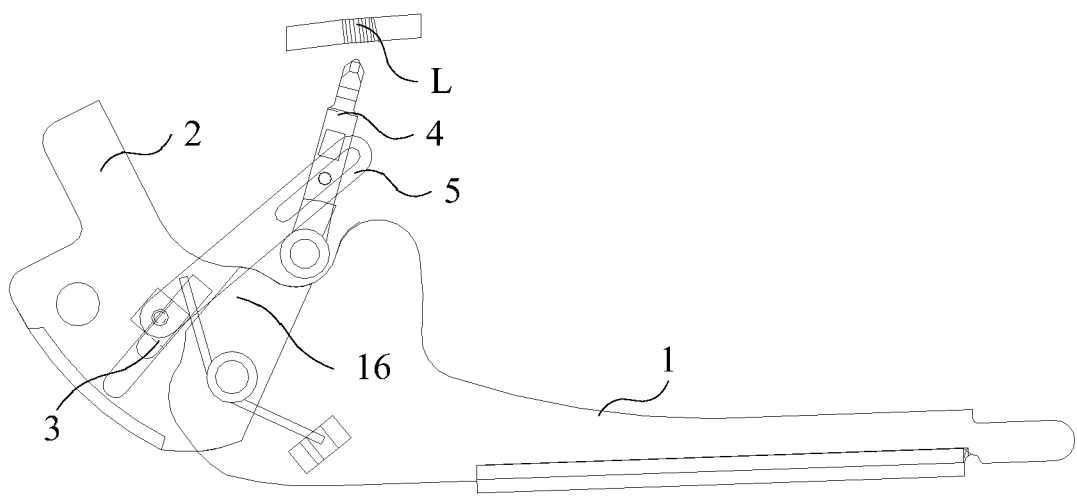
FIG. 14 is a schematic view of the handle assembly when the indicator is in the second position area, and the first handle is rotated, according to another embodiment of the present disclosure.
Figure 15:
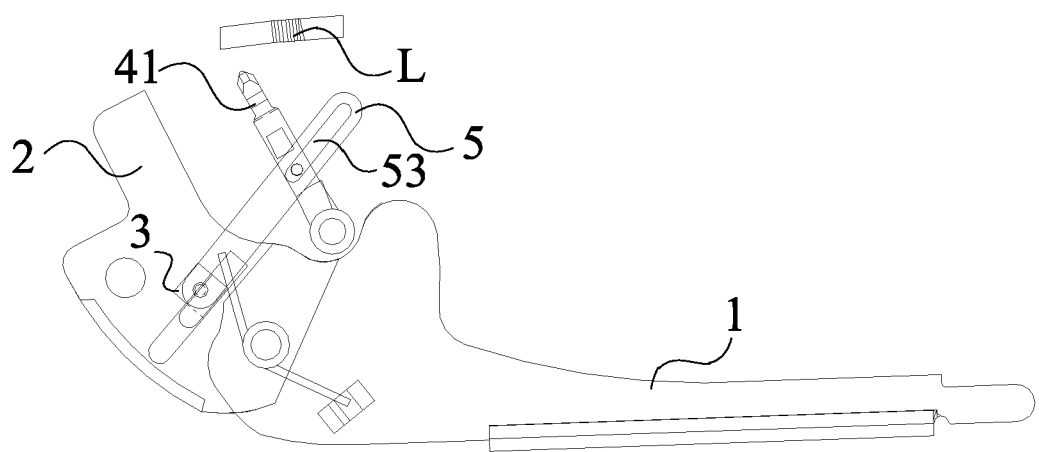
FIG. 15 is a schematic view of the handle assembly when the indicator returns to its initial position after the second handle is actuated by the first handle, according to another embodiment of the present disclosure.

As shown in FIG. 13, the first end 41 of the indicator 4 is moved to the second position area L by the pulling sheet, and the first handle 1 is not pressed. The slider 3 is moved to the second section of the slot 26 by the indicator 4 and the rod 5, and will interfere with the handle butting portion 16. As shown in FIG. 14, when the first handle 1 is pressed to rotate, the handle butting portion 16 will be in contact with the slider 3, to realize the linkage between the first handle 1 and the second handle 2. Therefore, the second handle 2 will be rotated anticlockwise, to push the staple pushing rod 65, thereby firing the stapler. After the stapler is fired, the state of the handle assembly when the indicator 4 is returned and the first handle 1 is not returned is shown in FIG. 15. The returning processes of the indicator 4, the first handle 1 and the second handle 2 are similar to those in the first embodiment as aforementioned, and similar description will be omitted here.

The present disclosure further provides a stapler, including the handle assembly. When the stapler is not ready to be fired, the second handle cannot be actuated by the first handle, and the stapler won't be fired. The doctor can also judge whether the stapler is ready to be fired or not according to his operation experience. The second handle can only be actuated by the first handle when the stapler is ready to be fired, to fire the stapler. Therefore, the stapler is prevented from being fired by mistake, and the casing of the stapler is prevented from being cracked at the same time.

The handle assembly and the stapler including the same has the following advantages.

In the present disclosure, the handle assembly includes a first handle and a second handle, and only the movement of the second handle can fire the stapler to cut and suture tissues; during operation, the first handle can be pressed by the doctor to move no matter whether the stapler is ready to be fired or not, while, the stapler cannot be fired by the first handle through the second handle when the stapler is not ready to be fired. The doctor can judge whether the stapler is ready to be fired or not according to his operation experience. The stapler can only be fired by the first handle through the second handle when the stapler is ready to be fired. The casing can be prevented from being cracked by pressing the handle vigorously, and the operators' experience is improved.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A handle assembly for firing a stapler, comprising:
   a first handle and a second handle;
   a slot, provided in the second handle and comprising a first section and a second section;
   a slider, slidably located in the slot; and
   wherein, when the slider is in the first section of the slot, and the first handle is rotated in a first direction, the slider is not in contact with the first handle, and the second handle is in an insurance position;
   when the slider is in the second section of the slot, and the first handle is rotated in the first direction, the slider is in contact with the first handle and actuates the second handle to move from the insurance position to a firing position.

2. The handle assembly according to claim 1, wherein, the handle assembly further comprises:
   an indicator, movable between a first position area and a second position area;
   a rod, having a first end connected to the indicator.

3. The handle assembly according to claim 2, wherein, a second end of the rod is connected to the slider, when the indicator is moved from the first position area to the second position area, the indicator actuates the slider to move from the first section to the second section of the slot through the rod.

4. The handle assembly according to claim 2, wherein, the indicator is connected to a distal end of a pulling sheet, a proximal end of the pulling sheet is sleeved on a screw rod, and a distal end of the screw rod is connected to a knob, when the knob is rotated to pull the pulling sheet to move towards a proximal end of the stapler, the indicator is moved by the pulling sheet from the first position area to the second position area.

5. The handle assembly according to claim 1, wherein, the first handle is rotatably connected to the second handle through a first pin, and the second handle is rotatably connected to a casing of the stapler through a second pin.

6. The handle assembly according to claim 5, wherein, a first torsion spring and a second torsion spring are sleeved on the first pin and the second pin, respectively; two ends of the first torsion spring are in contact with the first handle and the second handle, respectively; two ends of the second torsion spring are in contact with the second handle and the casing of the stapler, respectively.

7. The handle assembly according to claim 2, wherein, the slider comprises a slider butting portion and a rod connecting portion, the rod connecting portion is connected to a second end of the rod; when the slider is in the second section of the slot, and the first handle is rotated in a first direction, the first handle is in contact with the slider butting portion.

8. The handle assembly according to claim 7, wherein, the rod connecting portion comprises a limit groove for the rod and a boss connected to the rod, the second end of the rod is inserted into the limit groove, and the rod is connected to the boss through a fastener.

9. The handle assembly according to claim 8, wherein, a pin-hole is provided on the boss, a connecting pin passes through the pin-hole, and the rod is rotatably connected to the boss through the connecting pin.

10. The handle assembly according to claim 7, wherein, the first handle comprises a handle butting surface, the slider butting portion comprises a slider butting surface, and when the first handle is in contact with the slider, the handle butting surface is parallel and fit to the slider butting surface.

11. The handle assembly according to claim 3, wherein, a groove for the rod is provided on the indicator, the first end of the rod is movably located in the groove for the rod.

12. The handle assembly according to claim 3, wherein, a groove for the indicator is provided on the rod, a first end of the indicator is movably located in the groove for the indicator.

13. The handle assembly according to claim 1, wherein, the first handle comprises a first cavity having two side walls, and the second handle comprises a second cavity having two side walls;
when the slider is in the first section of the slot, and the first handle is rotated in the first direction, the first handle at least partially enters into the second cavity; when the slider is in the second section of the slot, and the first handle is rotated in the first direction, end surfaces of the side walls of the first handle is in contact with the slider, to prevent the first handle from continuing to enter into the second cavity.

14. The handle assembly according to claim 6, wherein, a limit groove for the first torsion spring is provided on the slider, two ends of the first torsion spring are in contact with the inner surface of the limit groove for the first torsion spring and the first handle, respectively.

15. The handle assembly according to claim 2, wherein, the handle assembly further comprises a return spring for the slider, when the slider is in the second section of the slot, the return spring is forced by the slider to be in a deformation state; when the return spring recovers from the deformation state to its initial state, the slider is actuated thereby to move from the second section to the first section of the slot.

16. The handle assembly according to claim 15, wherein, the return spring is a return torsion spring for the slider, a limit groove for the return torsion spring is provided on the slider, and two ends of the return torsion spring are in contact with the inner surface of the limit groove for the return torsion spring and the first handle.

17. The handle assembly according to claim 16, wherein, the slider further comprises a slider butting portion and a rod connecting portion connected to a second end of the rod, the limit groove for the return torsion groove is located between the slider butting portion and the rod connecting portion; when the slider is in the second section of the slot, and the first handle is rotated in a first direction, the first handle is in contact with the slider butting portion.

18. A stapler, comprising the handle assembly according to claim 1.

* * * * *